United States Patent
Becker et al.

(10) Patent No.: US 9,585,731 B2
(45) Date of Patent: Mar. 7, 2017

(54) ENDODONTIC FILE HAVING AN OUTER SPIRAL CORD

(71) Applicant: Medic NRG Ltd., Kibbutz Afikim (IL)

(72) Inventors: Arik Becker, Kibbutz Afikim (IL); Shlomo Berkovich, Herzeliya (IL); Haim Levy, Pardes Hana (IL)

(73) Assignee: Medic NRG Ltd., Kibbutz Afikim (IL)

( * ) Notice: Subject to any disclaimer, the term of this patent is extended or adjusted under 35 U.S.C. 154(b) by 204 days.

(21) Appl. No.: 14/360,328

(22) PCT Filed: Nov. 22, 2012

(86) PCT No.: PCT/IL2012/000380
§ 371 (c)(1),
(2) Date: May 23, 2014

(87) PCT Pub. No.: WO2013/076717
PCT Pub. Date: May 30, 2013

(65) Prior Publication Data
US 2014/0329199 A1 Nov. 6, 2014

(30) Foreign Application Priority Data

Nov. 24, 2011 (IL) .......................................... 216587

(51) Int. Cl.
*A61C 5/02* (2006.01)
(52) U.S. Cl.
CPC .................................... *A61C 5/023* (2013.01)
(58) Field of Classification Search
CPC ..................................................... A61C 5/023
(Continued)

(56) References Cited

U.S. PATENT DOCUMENTS

| 1,168,052 A | 1/1916 | Bolls |
| 1,771,182 A | 7/1930 | Lentulo |

(Continued)

FOREIGN PATENT DOCUMENTS

| EP | 1779804 A2 | 5/2007 | |
| IL | WO 2008102352 A1 * | 8/2008 | ............. A61C 5/023 |

(Continued)

OTHER PUBLICATIONS

International Search Report and Written Opinion for International Application No. PCT/IL2011/000179 dated Jul. 20, 2011.

(Continued)

*Primary Examiner* — Matthew Nelson
(74) *Attorney, Agent, or Firm* — Dinsmore & Shohl LLP (57) ABSTRACT

An endodontic file (10) has a handle (11) and a spiral cord (15) of helically wound metallic wire wound in a predetermined direction around a central metallic cord (13) formed between opposite ends of the central cord so as to form an integrated structure (18) of generally conical cross-section including a narrow tip end (17) and an opposite wider upper end (16) supported at the upper end by the handle. A flexible conical reinforcement (26, 31) supported by the handle covers an outermost layer of an upper portion of the spiral cord remote from the tip end, its lower end being of sufficiently low diameter to enter the root canal and dimensioned at its upper end to limit bending of the upper portion. An outer surface (20) of the spiral cord is configured for removing material from inside the root canal when the endodontic file is rotated in the predetermined direction.

14 Claims, 5 Drawing Sheets

(58) Field of Classification Search
USPC ................................. 433/102, 141–143, 224
See application file for complete search history.

(56) References Cited

U.S. PATENT DOCUMENTS

| | | | |
|---|---|---|---|
| 2,611,960 A | 9/1952 | Herndon | |
| 3,306,375 A | 2/1967 | Macks | |
| 3,330,040 A * | 7/1967 | Kahn | A61C 5/023 433/102 |
| 3,850,054 A | 11/1974 | Weissman | |
| 3,884,230 A | 5/1975 | Wulff | |
| 4,145,061 A | 3/1979 | Schneider | |
| 4,185,388 A | 1/1980 | Jarby | |
| 4,190,958 A | 3/1980 | Martin et al. | |
| 4,202,101 A | 5/1980 | Weissman | |
| 4,292,027 A | 9/1981 | Richmond | |
| 4,447,208 A | 5/1984 | Kawai | |
| 4,636,171 A | 1/1987 | Martin | |
| 4,830,615 A | 5/1989 | Goldstein et al. | |
| 4,850,867 A | 7/1989 | Senia et al. | |
| 5,211,560 A | 5/1993 | Lowder et al. | |
| 5,254,004 A * | 10/1993 | Feldman | A61C 1/141 433/129 |
| 5,334,020 A | 8/1994 | Eckert | |
| 5,482,461 A | 1/1996 | Yale | |
| 5,516,287 A | 5/1996 | Zdarsky | |
| 5,533,897 A | 7/1996 | Zdarsky | |
| 5,775,903 A | 7/1998 | Atkins | |
| 5,915,964 A | 6/1999 | Walia | |
| 6,179,617 B1 | 1/2001 | Ruddle | |
| 6,213,771 B1 | 4/2001 | Fischer | |
| 6,443,730 B2 | 9/2002 | Davidson | |
| 6,464,498 B1 | 10/2002 | Pond | |
| 6,575,748 B1 | 6/2003 | Filhol | |
| 6,579,092 B1 * | 6/2003 | Senia | A61C 5/023 433/102 |
| 6,589,052 B1 * | 7/2003 | Wilcko | A61C 5/023 433/102 |
| 6,746,245 B2 | 6/2004 | Riitano et al. | |
| 6,966,774 B2 | 11/2005 | Brock et al. | |
| 6,981,869 B2 | 1/2006 | Ruddle | |
| 7,137,815 B2 | 11/2006 | Matsutani et al. | |
| 7,226,289 B2 | 6/2007 | Bills | |
| 2003/0203155 A1 | 10/2003 | Kobe et al. | |
| 2005/0026109 A1 | 2/2005 | Buchanan | |
| 2005/0221256 A1 | 10/2005 | Kangasneimi | |
| 2006/0110704 A1 * | 5/2006 | Bills | A61C 5/023 433/102 |
| 2006/0127843 A1 | 6/2006 | Rosenblood et al. | |
| 2006/0216668 A1 | 9/2006 | Scianamblo | |
| 2007/0015107 A1 | 1/2007 | Mannschedel et al. | |
| 2007/0099149 A1 * | 5/2007 | Levy | A61C 5/023 433/102 |
| 2007/0101827 A1 | 5/2007 | Quan et al. | |
| 2010/0105004 A1 * | 4/2010 | Levy | A61C 5/023 433/102 |
| 2011/0033821 A1 * | 2/2011 | Rzhanov | A61C 5/023 433/102 |
| 2011/0033822 A1 * | 2/2011 | Bahcall | A61C 5/023 433/102 |
| 2011/0212413 A1 * | 9/2011 | Becker | A61C 5/023 433/102 |
| 2013/0260334 A1 * | 10/2013 | Pernot | A61C 5/04 433/81 |

FOREIGN PATENT DOCUMENTS

| | | |
|---|---|---|
| WO | 2008102321 A2 | 8/2008 |
| WO | 2008102352 A1 | 8/2008 |
| WO | 2011104705 A1 | 9/2011 |

OTHER PUBLICATIONS

International Search Report and Written Opinion for International Application No. PCT/IL2012/000139 dated Sep. 6, 2012.
International Preliminary Report on Patentability for International Application No. PCT/IL2012/000139 dated Jul. 5, 2013.
International Preliminary Report on Patentability for International Application No. PCT/IL2012/000380 dated Mar. 12, 2014.

* cited by examiner

ENDODONTIC FILE HAVING AN OUTER SPIRAL CORD

FIELD OF THE INVENTION

The present invention relates to an endodontic file adapted for rotation by a motorized dental handpiece.

BACKGROUND OF THE INVENTION

US20070099149 entitled "Endodontic device and method of utilizing and manufacturing same" corresponding to IL 171705 in the name of the present applicant discloses an endodontic device for cleaning, filing or reaming root canals. The device includes one or more metallic, flexible strands having an edge, a working section, a connecting section and a coupling head connected thereto. The wire strands are coated along the working section with a thin layer of a binder having abrasive particles embedded therein. In the file disclosed by US20070099149 the flexible, longitudinal strands are so constructed that their outer surfaces serve as active filing surfaces.

The invention described in this publication heralded a series of improvements, some of which are described in WO 2008/102352 entitled "Endodontic File" and WO 2011/104705 entitled "Rotary Endodontic File with Frictional Grip".

Common to both these publications is an endodontic file for use with a dental instrument having at least one cord and a helical wire wound around at least a major portion of the cord and having an abrasive outer surface. In WO 2011/104705 the handle is adapted to be gripped in a handpiece by friction alone. This act as a safety clutch that helps to prevent fracture of the endodontic file should it snag inside the root canal, since once the force required to rotate the drill exceeds the friction of the clutch, the tool can no longer rotate.

In some prior art endodontic files, it is known to make the central cord so rigid that the inner cord can unintentionally penetrate the side wall of the root canal during the root canal procedure.

In WO 2011/104705 the handle is formed separate from the file portion with a hollow bore as best shown in FIG. 2 thereof and the upper end of the file portion is bonded within the hollow bore. As well shown in FIG. 7 thereof, the central cord of the file portion is of slightly smaller diameter than the internal diameter of the helical coil, so that it is free to slide within the helical coil. This requires that the upper end of helical coil be fixedly attached to the end of the cord, for example by tightly coiling a few turns of the helical wire around the end of the cord as shown in FIGS. 2 and 3 prior to attachment of the handle. Furthermore, as best shown in FIGS. 2 and 3, the central cord protrudes forward of the helical wire toward the working or tip end of the endodontic file by a length of 3 to 6 mm. The central cord at the tip end of the file may be treated to form a globule such that the tip of the file serves as a guide, rather like a mole's snout, for guiding the file through a pre-formed cavity as shown in FIG. 5. However, the small diameter of the cord, typically 0.2-0.3 mm, and its relative rigidity, render the file subject to penetration through the wall of the dental cavity.

Conventional approaches to forming an abrasive surface are as described in WO 2008/102352 where an abrasive layer is composed of a binder containing abrasive particles and is then coated on the outer surface of the file. It has been found during use of such files that the small abrasive particles can separate from the binder and become dislodged in the tooth canal, which is obviously undesirable.

SUMMARY OF THE INVENTION

According to a first aspect of the invention there is provided an endodontic file comprising:

a handle adapted for attaching to a motorized handpiece configured for rotation in a predetermined direction of rotation;

a spiral cord comprising a layer of helically wound wire formed of a metallic material wound in said predetermined direction of rotation around a central cord formed of a metallic material between opposite ends of the central cord so as to form an integrated structure that retains contact between the spiral cord and the central cord during rotation of the endodontic file within a root canal;

said integrated structure having a generally conical cross-section including a narrow tip end and an opposite wider upper end and being supported at the upper end by the handle; and a flexible reinforcement protruding from and supported by the handle covering an outermost layer of an upper portion of the spiral cord remote from the tip end of the integrated structure, said flexible reinforcement being conical in cross-section and of sufficiently low diameter at a lower end thereof to enter the root canal and having a sufficiently high diameter at its upper end to limit bending of said upper portion;

an outer surface of the spiral cord being configured for removing material from a wall of the root canal upon rotation of the endodontic file within the root canal in said predetermined direction.

According to a second aspect of the invention there is provided a method for manufacturing an endodontic file for use with a motorized handpiece that is configured for rotation in a predetermined direction of rotation, the method comprising:

winding a spiral cord around and between opposite ends of a central cord formed of a metallic material in said predetermined direction of rotation, said spiral cord comprising a layer of helically wound wire formed of a metallic material so as to form an integrated structure having a generally conical cross-section including a narrow tip end and an opposite wider upper end and wherein contact is retained between the spiral cord and the central cord during rotation of the endodontic file within a root canal;

fixedly attaching to an upper end of the integrated structure a handle adapted for gripping by a motorized handpiece;

supporting from the handle a flexible reinforcement covering an outermost layer of an upper portion of the spiral cord remote from the tip end of the integrated structure, said flexible reinforcement being conical in cross-section and of sufficiently low diameter at a lower end thereof to enter the root canal and having a sufficiently high diameter at its upper end to limit bending of said upper portion; and configuring an outer surface of the spiral cord for removing material from a wall of the root canal upon rotation of the endodontic file within the root canal in said predetermined direction.

According to a third aspect of the invention there is provided an endodontic file comprising:

an integrated structure comprising a spiral cord formed of a metallic material wound in a predetermined direction of rotation around a central cord formed of a metallic material between mutually opposite first and second ends of the integrated structure;

a handle fixed to the first end of the integrated structure and being adapted for rotation in said predetermined direction of rotation by a motorized handpiece; and an outer surface of the spiral cord being configured for removing material from a wall of the root canal upon rotation of the endodontic file within the root canal in said predetermined direction by spraying tiny metal grains at high pressure so as to produce a rough textured surface.

According to a fourth aspect of the invention there is provided a method for manufacturing an endodontic file for use with a motorized handpiece that is configured for rotation in a predetermined direction of rotation, the method comprising:

winding a spiral cord formed of a metallic material around a central cord formed of a metallic material in said predetermined direction of rotation so as to form an integrated structure that retains contact between the spiral cord and the central cord during rotation of the endodontic file within a root canal;

fixedly attaching a handle adapted for gripping by a motorized handpiece to the integrated structure at a first end thereof; and spraying tiny metal grains at high pressure on an outer surface of the spiral cord so as to roughen said outer surface for removing material from a wall of the root canal upon rotation of the endodontic file within the root canal in said predetermined direction.

In some embodiments, the central cord and spiral cord are formed together in a continuous process by continuously withdrawing the cord from a feed-station and winding the spiral cord around the cord as it is withdrawn; the central cord and surrounding spiral cord being cut at predetermined intervals of time to form multiple discrete integrated structures to each of which a respective handle is then attached. However, the invention also contemplates forming the central cord and spiral cord independently in separate stages and assembling one or more spiral cords on a preformed central cord.

In some embodiments of the invention, the spiral cord comprises a single helical winding whose outer surface is abraded. In some embodiments, the spiral cord is wound on a highly flexible core of diameter, which may be in the range of 0.12 to 0.22 mm, according to the desired flexibility for the operation to be performed in the canal and comprises an inner helical winding of narrow diameter wire, typically 0.12 to 0.20 mm around which there is wound an outer helical winding of larger diameter wire, typically 0.15 to 0.50 mm according to the desired flexibility for the operation to be performed in the canal. The file is tapered from the handle to the tip so as to progressively remove the outer helical winding toward the tip but leaving the inner winding intact. Likewise, the outer diameter of the spiral winding at its widest point should be sufficient to provide enough strength to remove material from the dental cavity at its widest opening. Consequently, the diameter of the spiral cord near the handle, where the outer winding is completely intact, is equal to the core diameter+2×($\phi$ of inner winding)+2×($\phi$ of outer winding) i.e. at least 0.16+0.32+0.6=1.08 mm and provides high flexibility. The outer surface of the spiral cord is ground to form a long and uniform surface which is then and abraded to facilitate the preparation of a conical channel in one or two passes of the file within the root canal.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2a is a pictorial elevation of an endodontic file according to an embodiment of the invention;

FIG. 2b is a cross-sectional view of the endodontic file through the line B-B in FIG. 2a;

FIG. 4b is a cross-sectional view of the endodontic file in FIG. 4a;

FIG. 5b is a cross-sectional view of the endodontic file in FIG. 5a;

FIG. 7b is a cross-sectional view of the endodontic file shown in FIG. 7a.

DETAILED DESCRIPTION OF EMBODIMENTS

In the following description of some embodiments, identical components that appear in more than one figure or that share similar functionality will be referenced by identical reference symbols.

Figure 1:
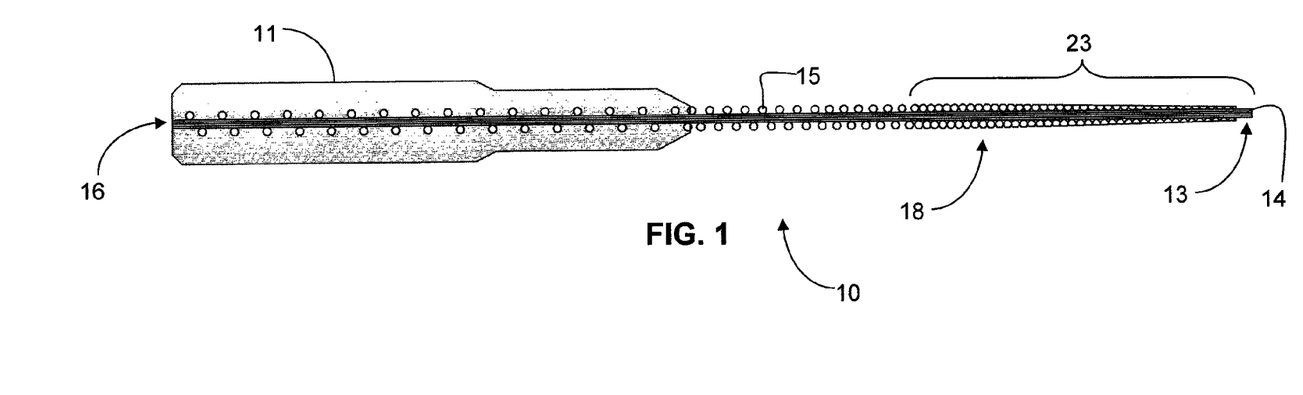
FIG. 1 is a pictorial cross-sectional view of an endodontic file according to an embodiment of the invention.

FIG. 1 is a cross-sectional view of an endodontic file 10 comprising a handle 11 adapted for attaching to a motorized handpiece (not shown) configured for rotation in a predetermined direction of rotation, typically clockwise. The endodontic file 10 has a central cord 13 that may be formed of multiple strands 14 of a suitable metallic material such as, for example, stainless steel around which a spiral cord 15 is wound in the predetermined direction of rotation between a first end 16 of the cord and an opposing second end thereof constituting a tip 17 of the file. This forms an integrated structure 18 that retains contact between the spiral cord 15 and the central cord 13 during rotation of the endodontic file within a root canal. The integrated structure 18 is supported at the first end 16 thereof by the handle 11 and the central cord 13 is slightly exposed from the spiral cord 15 at the tip 17. Typically, the tip 17 is exposed for a length of up to 0.5 mm.

Figures 2A, 2B:
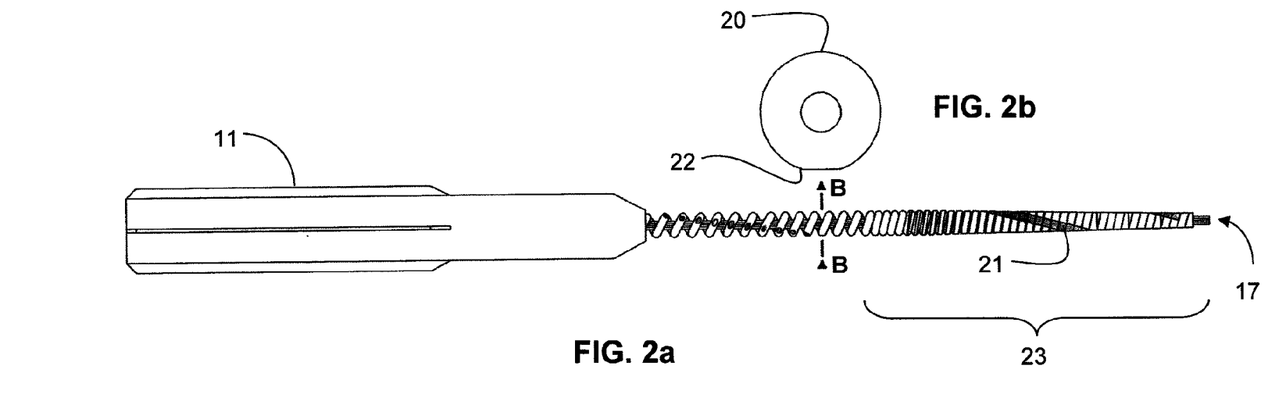

In order to vary the flexibility of the resulting structure, the pitch of the helically wound coiled cord 15 may be varied. Specifically, the more closely the helix is wound, the more flexible is the file and vice versa. Higher rigidity is required where the file protrudes from the handle 11, and to this end the pitch of the spiral cord is increased as shown in FIG. 2a. Toward the tip 17, high flexibility is desirable and the pitch is reduced so that adjacent coils are contiguous.

An outer surface 20 of the spiral cord 15 is configured for removing material from a wall of the root canal upon rotation of the endodontic file within the root canal in the predetermined direction. This may be done by treating the outer surface 20 of the spiral wire to form an abrasive surface. Additionally or alternatively as seen in FIG. 2a, a fluted channel 21 may be cut longitudinally through the outer surface of the spiral cord 15 forming a flat surface having sharp corners 22 shown in FIG. 2b that act as cutting edges when the endodontic file is rotated inside the root canal. The fluted channel 21 is cut with an orientation that is opposite to the direction of rotation so that during use of the file, tooth residue is removed from the root canal through the fluted channel.

The central cord is typically formed of multiple twisted strands of a suitable metallic material such as stainless steel as described in more detail below. In some embodiments, the handle 11 is injection molded or pressure fitted directly on to the integrated structure 18 and is secured by the helically wound cord 15 which interlocks with complementary grooves formed in the handle when the handle solidifies or cures. The handle 11 may be formed of an elastomeric material that is adapted for gripping by a chuck of the motorized handpiece by friction alone, thereby acting as a safety clutch that helps to prevent fracture of the endodontic file should it snag inside the root canal, as explained above.

Owing to the above-described construction, the spiral cord 15 may be bound to the central cord 13 by friction alone, thus obviating the need for additional securing such as twisting as is required in WO 2011/104705 where the central cord is of smaller gauge than the spiral wire, which must be secured or bonded to the central cord at the handle-end prior to insertion within the hollow bore of the handle. In accordance with some embodiments of the invention, this additional manufacturing step is avoided owing to the spiral wire being so tightly wound around the central cord that together they form an inseparable integrated structure. Moreover, since the molded handle forms complementary grooves around the spiral wire, the integrated structure is retained firmly in the handle without the need for additional bonding or twisting. In accordance with other embodiments, the spiral wire is wound sufficiently loosely to leave some minimal play between the spiral winding and the central core, which is reduced during actual use owing to the screwing action of the spiral winding against the internal surface of the tooth canal.

The forces applied to the file 10 are split into two components:
1. A horizontal component that applies pressure to the canal walls due to the flexibility of the file and the centrifugal forces reached at 10-12,000 RPM.
2. A vertical component that pushes the file forward toward the apical constriction.

It has been found in practice that the flexibility of the file as well as the two force components enable the file to adapt well to the canal's oval shape.

Figure 3A:
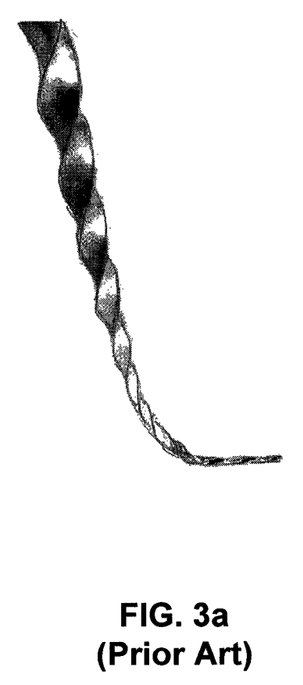
FIG. 3a is a pictorial view showing deformation of a prior art Ni—Ti endodontic file.
Figure 3B:
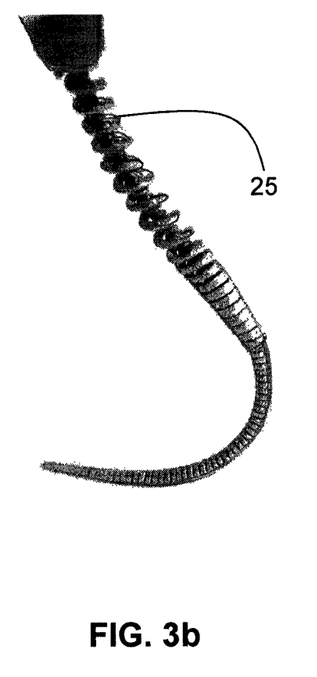
FIG. 3b is a pictorial view showing deformation of embodiments of the endodontic file having two layers of spiral windings according to an embodiment of the invention.

FIG. 3a is a pictorial view showing deformation of a prior art Ni—Ti endodontic file. As is seen, only the tip of the file is amenable to deformation and, even then, the degree of bending is minimal. As opposed to this, FIGS. 3b and 3c show that the file according to the invention may be bent sharply without compromising its strength and, most significantly, without risking fracture at the point where the file protrudes from the handle, where it is most vulnerable.

In one embodiment reduced to practice the central cord 13 comprised a plurality of strands each of diameter between 0.12 to 0.22 mm and the spiral cord 15 was formed of wire having a diameter between 0.15 to 0.50 mm wound directly on to the central cord with varying pitch. In one embodiment, the central cord was constructed by twisting multiple strands of diameter between 0.12 and 0.22 mm in the direction of rotation of the file around a single wire of similar diameter. In another embodiment, the central cord 13 was formed by twisting multiple strands of diameter between 0.12 and 0.22 mm against the direction of rotation of the file around a single wire of diameter between 0.14 and 0.18 mm, followed by twelve more strands twisted in the direction of rotation of the file.

The outer surface 20 of the spiral cord 15 is abraded to form an active portion 23 starting from where the adjacent coils of the spiral cord 15 become contiguous all the way down toward the tip 17 to form a frusto-conical portion having a length typically between 4 to 15 mm. The total length of the file is typically approximately 23 to 35 mm, so the active portion 23 is at most approximately one-third the length of the file. As seen in FIGS. 1 and 2a, the active portion 23 forms in cross-section a trapezium whose sides are constituted by the opposing edges of the file and whose top edge is the diameter of the file prior to abrasion. The relationship between the length of the conical portion and its diameter thus determines the apex angle of the tip. The core diameter also determines the gauge of file at it working end. As best seen in FIG. 1, the diameter of the file at the top edge of the active portion 23 is equal to the diameter of the central cord plus twice the diameter of the spiral cord 15, since a single turn of the spiral cord 15 adds to the overall width of the file on both sides of the central cord. It should be noted that these dimensions relate to the file prior to forming the conical taper. In order that the spiral core at the tip be sufficiently durable, it is desirable that its wall thickness at the narrowest point of the tip be no less than 0.04 mm. Consequently, if the diameter of the central cord at the tip is 0.12 mm, it follows that the outer diameter of the complete integrated structure will be no less than 0.2 mm.

An active area corresponding to approximately two-thirds of the exposed area of the file is covered with a rough textured surface created by spraying tiny metal grains at high pressure, typically during rotation of the file. When the file is rotated at high speed during use, this textured surface polishes the surface of the dentine. The size of the metal grains may be in the range 22 to 32 mesh.

In order to enhance flexibility without subjecting the file to the risk of fracture where it protrudes from the handle, there may further be provided a reinforced portion for limiting bending of the file in a region where the integrated structure protrudes from the handle. In FIG. 3b the reinforced portion is a wire 25 that is spirally wound an upper section of the integrated structure near the handle.

Figure 4A:
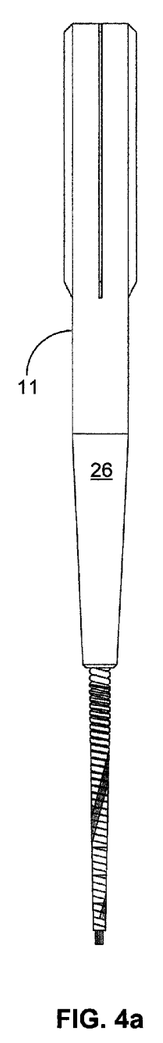
FIG. 4a is a pictorial elevation of an endodontic file according to an embodiment of the invention.
Figure 4B:
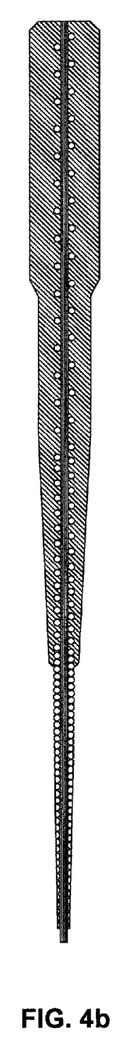

FIG. 4a is a pictorial elevation and FIG. 4b is a cross-sectional view of an endodontic file according to another embodiment similar to that shown in FIGS. 1 and 2a, but whose handle 11 is integrally molded with a sleeve 26 that covers an upper section of the integrated structure. The sleeve 26 constitutes a reinforced portion that is supported by the handle and covers an upper section of the integrated structure. The sleeve 26 is tapered and dimensioned such that at its lower end it is sufficiently narrow to enter the root canal. It is known to provide insulating sleeves on an upper end of endodontic files for the purpose of avoiding short-circuits when using apex locators. One such example is shown in US 2003/0064347 having a thin non-conductive sleeve of 0.02 mm to 0.04 mm wall thickness surrounding a conductive shank and longitudinally extending along the conductive shank. It should be noted, however, that the non-conductive sleeve provides no reinforcement since it is of a constant wall thickness, which is too low in a region proximate the handle to provide support. In the invention, the sleeve 26 is of conical cross-section ranging in wall thickness from approximately 0.03 mm at its thin end to 0.30 mm where it is supported by the handle and this reinforces the file near the cavity opening so that it can be bent with significantly reduced risk of fracture. This is also true, of course, when in those embodiments having a double spiral core where the outer spiral layer is supported by the handle and provides similar reinforcement. The narrow tip 17 allows the file to reach the narrow end of the root canal even when the root canal curves at a sharp angle that subjects the working end of the file to significant bending. This is rendered possible by virtue of:

Small diameter and high flexibility at the frusto-conical tip of the file;

Gradual rigidity of the remaining portion of the file allowing force applied vertically via the handpiece to achieve extended penetration;

Ability to maintain its deformed shape even at high speed (5000 to 15,000 rpm)

Ability to abrade the inner walls of the root canal while forming a conical canal structure that is particularly well-suited to sealing using gutta percha.

Ability to withdraw tooth residue out of the root canal via the fluted channel 21 by fluid irrigation between successive files during the process of preparing the canal and prevent it being pushed in and packed within the apical constriction.

In the embodiments described above, the spiral cord comprises a single helical winding whose outer surface is abraded. However, according to another embodiment shown in FIGS. 5*a* and 5*b*, the spiral cord 15 may comprise an inner helical winding 30 of narrow diameter wire as described above, around which there is then wound an outer helical winding 31 of larger diameter wire, typically 0.25 to 0.50 mm. In such an embodiment, the outer winding 31 constitutes a reinforced portion that is supported by the handle and covers an upper section of the integrated structure. Here also, the outer layer is tapered and dimensioned such that at its lower end it is sufficiently narrow to enter the root canal. In some embodiments, the outer layer is wound in a direction opposite to the direction of rotation and serves to channel debris removed from the inner wall of the cavity out of the root canal. The diameter of the central cord on which the inner helical winding 30 is wound is as low as 0.12 to 0.22 mm i.e. significantly less than that of the embodiment shown in FIGS. 1 and 2. The outer helical winding 31 significantly increases the flexibility of the file owing to the larger diameter of at least 1.1 mm relative to the thickness of the helical wire (0.25 mm to maximum 0.50 mm).

Figure 6A:
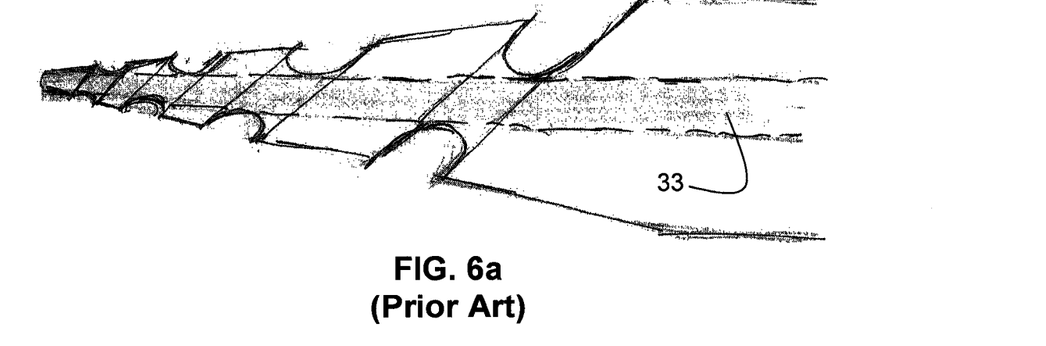
FIG. 6a is a pictorial representation showing a detail of the spiral winding of a prior art endodontic file.

FIG. 6*a* is a pictorial representation showing a detail of the spiral winding of a prior art endodontic file. It is seen that the spiral is wound on a central cord 33 having a right-cylindrical cross-section. This is similar in principle to a high-speed drill bit whose helical flutes are of equal diameter. It is seen that as the file penetrates further into the root canal and increasing amounts of debris are removed, the diameter of the helical flutes increases and thereby become more effective at removing the debris. What this means in practice is that as the tip of the file starts to penetrate the root canal and only a small quantity of material is removed, the helical flute at the tip is of minimal length but is sufficient to channel the small amount of tooth debris out of the root canal. As the endodontic file penetrates further, an increasing amount of debris is removed but the helical flute also increases in size and therefore remains an effective conduit for removing the debris. However, since the central cord remains of constant diameter it provides an equal degree of mechanical support throughout its length, which may not be sufficient to accommodate stresses imposed by anatomical features of the root canal. As the outer diameter of the integrated structure increases relative to the diameter of the central cord, the file has less ability to resist fatigue imposed by the increased torque applied by the cavity.

Figure 6B:
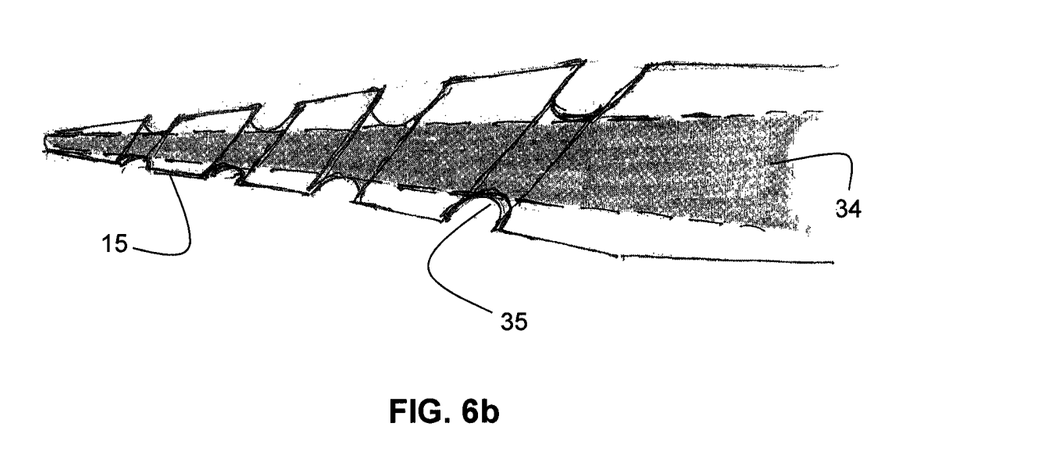
FIG. 6b is a pictorial representation showing a detail of the spiral winding of an endodontic file according to an embodiment of the invention.

FIG. 6*b* is a pictorial representation showing a detail of the spiral winding of an endodontic file according to an embodiment of the invention. In this case, the spiral cord 15 is wound on a central cord 34 of conical cross-section, such that the diameter of the helical flutes shown as 35 increases as the width of the file increases. Consequently, as the depth of the flute increases, it remains supported on a central core whose diameter likewise increases thus providing higher resistance to fatigue.

Figure 5A:
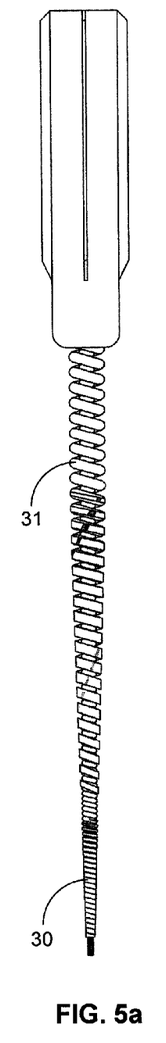
FIG. 5a is a pictorial elevation of an endodontic file according to an embodiment of the invention.
Figure 5B:
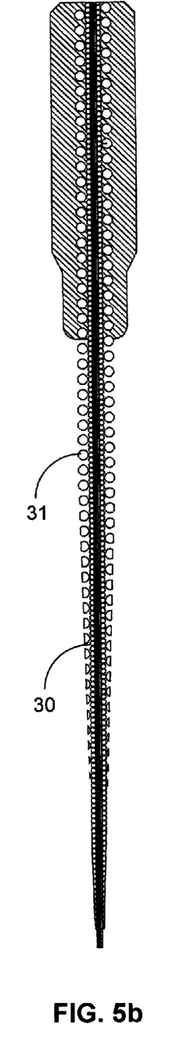
Figure 7A:
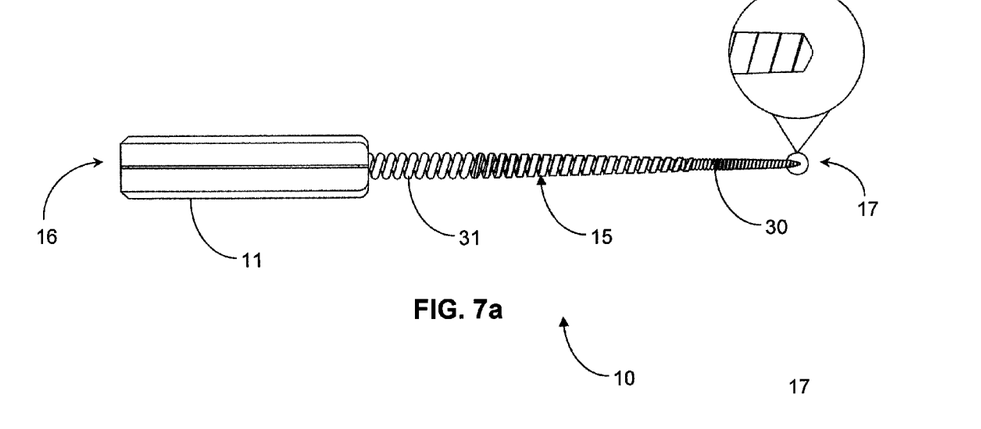
FIG. 7a is a pictorial elevation of an endodontic file according to an embodiment of the invention.
Figure 7B:
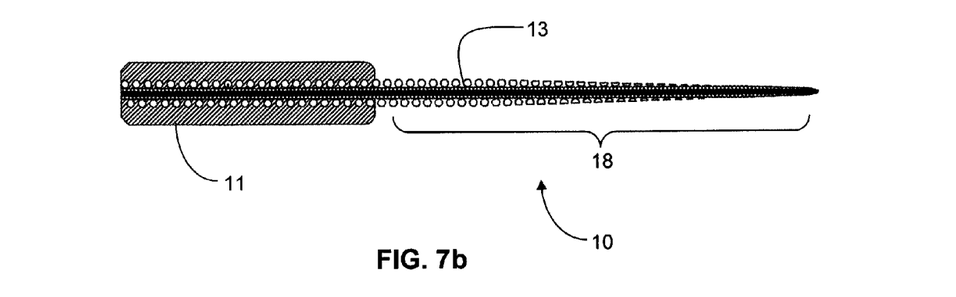

FIGS. 7*a* and 7*b* show, respectively, a pictorial elevation and a cross-sectional view of an endodontic file 10, according to a slight variation of the embodiment shown in FIGS. 5*a* and 5*b*. The endodontic file 10 comprises a handle 11 adapted for attaching to a motorized handpiece (not shown) configured for rotation in a predetermined direction of rotation, typically clockwise. The endodontic file 10 has a central cord 13 that may be formed of multiple strands of a suitable metallic material around which a spiral cord 15 is wound in the predetermined direction of rotation between a first end 16 of the cord and an opposing second end thereof constituting a tip 17 of the file. This forms an integrated structure 18 that retains contact between the spiral cord 15 and the central cord 13 during rotation of the endodontic file within a root canal. Note that while not shown by the arrow in the figure, the integrated structure 18 extends all the way into the handle 11 and is supported at the first end 16 thereof by the handle 11. Unlike the embodiment in FIG. 1, the central cord 13 is concealed by the spiral cord 15 at the tip 17. The spiral cord 15 is formed of a double layer of helically wound wire including an inner layer 30 and an outer layer 31 both formed of a metallic material, the outer layer having wire of larger diameter than the inner layer. The tip end 17 is chamfered to form a sharp point that serves as a navigator when directing the endodontic file through the tooth canal.

All of the exposed area of the file is covered with a rough textured surface created by spraying tiny metal grains at high pressure. When the file is rotated at high speed, this textured surface polishes the surface of the dentine. If the textured surface is formed after chamfering the tip end 17, the tip end 17 will also be abrasive. In this case, the tip is "active" that serves both to guide the endodontic file through a patient's root canal and to cut an inner wall thereof. Alternatively, the textured surface may be formed prior to chamfering the tip end 17, in which case the tip end 17 will not be abrasive and will serve only to guide the endodontic file through a patient's root canal.

It will be understood that the foregoing description describes several features that are mutually independent and may therefore be combined in different files. All such combinations as are encompassed by the appended claims are to be considered part of the invention as if they were described separately. Thus, by way of example, although the file shown and described in FIGS. 5*a* and 7*a* has a spiral cord composed of a double layer whose abrasive outer surface may be created by spraying tiny metal grains at high pressure, these two features are mutually independent. Thus, the embodiment shown in FIG. 1, whose spiral cord does not employ a double layer, can nevertheless be provided with a roughened texture using this technique. On the other hand, the outer surface may be rendered abrasive by coating an abrasive layer composed of a binder containing abrasive particles and while this is not novel per se it may be used in combination with other features of the invention that are believed be novel.

It should also be noted that in all embodiments of the invention, it is important that the central cord be flexible. The desired flexibility is typically achieved using multiple strands of wire. However, a single wire or cable of sufficient flexibility may be employed instead.

The construction of the file according to the invention makes it possible to mass manufacture the file in a streamlined process where the central cord and spiral wire are formed together so as to produce a continuous length of material, which can then be segmented. This is a significant improvement over the process for manufacturing the file described in WO 2011/104705 where the spiral and the central cord must be formed separately and then assembled. The present invention allows the need for such assembly to be obviated.

In accordance with the invention, a method for manufacturing an endodontic file of the kind described above comprises spirally winding a wire tightly around a central cord in a predetermined direction of rotation so as to form an integrated structure that retains tight contact between the spiral wire and the central cord during rotation of the endodontic file within a root canal. If desired, the speed at which the central cord is withdrawn during winding of the spiral wire may be varied, so as to vary the pitch of the spiral winding. To a required length of the integrated structure there is then fixedly attached a handle adapted for attaching to a motorized handpiece, and an outer surface of the spiral wire is configured for removing material from a wall of the root canal upon rotation in the predetermined direction of the endodontic file within the root canal.

The manner in which spiral wire is wound comprises continuously withdrawing the cord from a feed-station and spirally winding the wire around the cord as it is withdrawn so as to form a continuous length of integrated structure. The cord and spirally wound wire are then cut at predetermined intervals of time to form multiple discrete integrated structures to each of which a respective handle is then attached. At the tip end of each file, the central is smooth and passive with round tip. According to some approaches, this may be performed after abrading an outer surface of the file near the tip end. In this case, chamfering the end of the file to form the tip will result in the tip having no abrasive surface and thus serving only as a navigator. According to an alternative approach, the file may first be shaped and then the outer surface abraded. In this case, the tip also will be abrasive and capable of cutting. Handles are then fixedly attached to each file, typically by injection molding or pressure fitting the handle on to the integrated structure.

Novel features of the invention include the following:
Combination of the central cord and spiral cord to form a single integrated and highly flexible structure, the respective properties of each of whose constituent parts complement each other and allow a root canal to be safely and effectively finished using a set of 2 to 5 endodontic files while maintaining the anatomical structure of the root channel without forcing the root canal to assume the shape of the endodontic files as so often happens with Nickel-Titanium (NiTi) endodontic files whose flexibility is confined only to the very tip of the file.
The endodontic file is particularly well suited to gradual successive widening of the root canal by appropriate change of the relationship between the diameter of the endodontic files and the pitch of the spiral winding and cone angle.

Method of Use:
The root canal is widened gradually using a set of files initially in "Crown Down" mode (i.e. working down from the cusp to the apical constriction) starting with the widest file and finishing with the most narrow.
The root canal is then filed in "Crown Up" mode increasing gradually from the narrowest file to the widest.
If necessary this cycle may be repeated. The filing with each file takes only a few seconds with the time preferably being controlled by a dedicated handpiece.
The entire process takes place after first injecting into the channel lubricant and disinfectant as conventionally used in root canal procedure such as RC-PREP or GLIDE and/other similar materials. Between each filing, the root canal is flushed using sodium hypo chloride or other suitable washing agent.

The invention claimed is:

1. An endodontic file comprising:
a handle adapted for attaching to a motorized handpiece configured for rotation in a predetermined direction of rotation;
a spiral cord comprising an inner helical winding formed of a metallic material wound in said predetermined direction of rotation around a central cord formed of a metallic material between opposite ends of the central cord so as to form an integrated structure that retains contact between the spiral cord and the central cord during rotation of the endodontic file within a root canal;
said integrated structure having a generally conical cross-section including a narrow tip end and an opposite wider end and being supported at the wider end by the handle; and
an outer surface of the spiral cord having an abrasive surface operable for removing material from a wall of the root canal upon rotation of the endodontic file within the root canal in said predetermined direction;
wherein the spiral cord comprises the inner helical winding of narrow diameter wire that constitutes a helically wound wire and is wound in said predetermined direction of rotation between the wider end of the spiral cord and the tip end of the endodontic file; and
wherein the spiral cord further comprises a reinforced portion comprising an outer helical winding of larger diameter wire wound around the inner helical winding being supported by the handle and covering at least an upper section of the integrated structure and having an active portion that extends towards the tip and has an abrasive outer surface.

2. The endodontic file according to claim 1, wherein the outer helical winding is wound in a direction opposite to said predetermined direction of rotation.

3. The endodontic file according to claim 1, wherein the central cord is exposed at the tip end of the file for a length of up to 0.5 mm.

4. The endodontic file according to claim 1, wherein the abrasive surface is created by spraying tiny metal grains at high pressure.

5. The endodontic file according to claim 1, wherein the handle is molded on to the integrated structure and is secured by the spiral cord which interlocks with complementary grooves formed in the handle when the handle solidifies or cures.

6. The endodontic file according to claim 1, wherein the central cord comprises multiple strands.

7. The endodontic file according to claim 6, wherein the strands are twisted.

8. The endodontic file according to claim 1, wherein the central cord comprises a single wire or cable.

9. The endodontic file according to claim 1, wherein the spiral cord includes the inner helical winding of varying pitch.

10. The endodontic file according to claim 9, wherein the pitch of the inner helical winding of the spiral cord is smaller toward the tip end than toward the wider end.

11. The endodontic file according to claim 1, wherein the handle is injection molded or pressure fitted on to the integrated structure.

12. The endodontic file according to claim 1, wherein the handle is formed of an elastomeric material that is adapted for gripping by a chuck of the motorized handpiece by friction alone.

13. The endodontic file according to claim 1, wherein a longitudinal channel is cut through the outer surface of the spiral cord so as to form sharp corners that act as cutting edges when the endodontic file is rotated inside the root canal.

14. The endodontic file according to claim 1, wherein the flexible reinforcement has a wall thickness of approximately 0.03 mm at the narrow lower end to 0.30 mm where it is supported by the handle.

\* \* \* \* \*

UNITED STATES PATENT AND TRADEMARK OFFICE
CERTIFICATE OF CORRECTION

PATENT NO. : 9,585,731 B2  
APPLICATION NO. : 14/360328  
DATED : March 7, 2017  
INVENTOR(S) : Arik Becker et al.

Page 1 of 1

It is certified that error appears in the above-identified patent and that said Letters Patent is hereby corrected as shown below:

In the Claims

Column 10, Claim 1, Line 47:
"wherein the spiral cord further comprises a reinforced"
Should read:
--wherein the spiral cord further comprises a flexible reinforced--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*